United States Patent
Bajic et al.

(10) Patent No.: US 9,976,187 B2
(45) Date of Patent: May 22, 2018

(54) METHYLATION BIOMARKERS FOR PROSTATE CANCER

(71) Applicant: KING ABDULLAH UNIVERSITY OF SCIENCE AND TECHNOLOGY, Thuwal (SA)

(72) Inventors: Vladimir Bajic, Thuwal (SA); Hicham Mansour, Thuwal (SA); Roberto Incitti, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 59 days.

(21) Appl. No.: 14/408,238

(22) PCT Filed: Jun. 11, 2013

(86) PCT No.: PCT/IB2013/001887
§ 371 (c)(1),
(2) Date: Dec. 15, 2014

(87) PCT Pub. No.: WO2013/186633
PCT Pub. Date: Dec. 19, 2013

(65) Prior Publication Data
US 2015/0292025 A1  Oct. 15, 2015

Related U.S. Application Data

(60) Provisional application No. 61/659,239, filed on Jun. 13, 2012.

(51) Int. Cl.
*C07H 21/04* (2006.01)
*C12Q 1/68* (2018.01)
(52) U.S. Cl.
CPC ..... *C12Q 1/6886* (2013.01); *C12Q 2600/154* (2013.01); *C12Q 2600/172* (2013.01)

(58) Field of Classification Search
None
See application file for complete search history.

(56) References Cited

U.S. PATENT DOCUMENTS

| | | | |
|---|---|---|---|
| 2007/0141582 A1 | 6/2007 | Li et al. | |
| 2009/0215066 A1 | 8/2009 | Ahmed et al. | |
| 2010/0303795 A1* | 12/2010 | Sorensen | A61K 31/192 424/94.6 |
| 2014/0094380 A1* | 4/2014 | Sherlock | C12Q 1/6886 506/9 |

OTHER PUBLICATIONS

Written Opinion of the International Searching Authority dated Nov. 15, 2013, issued in International Application No. PCT/IB2013/001887.
International Search Report dated Nov. 15, 2013, issued in International Application No. PCT/IB2013/001887.
Notification Concerning Transmittal of International Preliminary Report on Patentability (Chapter I of the Patent Cooperation Treaty) dated Dec. 24, 2014, issued in International Application No. PCT/IB2013/001887.
Vanaja Donkena Krishna et al: "Hypermethylation of Genes for Diagnosis and Risk Stratification of Prostate Cancer", Cancer Investigation, vol. 27, No. 5, 2009, pp. 549-560, ISSN: 0735-7907.
Kim Jung H et al: "Deep sequencing reveals distinct patterns of DNA methylation in prostate cancer", Genome Research, Cold Spring Harbor Laboratory Press, Woodbu Ry, NY, US, vol. 21, No. 7, Jul. 1, 2011 (Jul. 1, 2011), pp. 1028-1041, XP009151377, ISSN: 1088-9051,DOI: 10.1101/GR.119347.110.

* cited by examiner

*Primary Examiner* — Jeanine A Goldberg
(74) *Attorney, Agent, or Firm* — Smith, Gambrell & Russell, LLP; Charles Vorndran

(57) ABSTRACT

Different combinations of methylation status based biomarkers can be used to test for prostate cancer with high sensitivity and high specificity.

2 Claims, No Drawings

METHYLATION BIOMARKERS FOR PROSTATE CANCER

This application claims the benefit of prior under 35 USC 371 to International Application No. PCT/IB2013/01887, filed Jun. 11, 2013, which claims priority to U.S. Provisional Application No. 61/659,236, filed Jun. 13, 2012, each of which is incorporated by reference in its entirety.

CLAIM OF PRIORITY

This application claims the benefit of prior U.S. Provisional Patent Application No. 61/659,236, filed on Jun. 13, 2012, which is incorporated by reference in its entirety.

TECHNICAL FIELD

This invention relates to methylation biomarkers for prostate cancer.

BACKGROUND

In term of new case per year, prostate cancer (PC) is currently ranked among the most frequent malignancy and is one of the major causes of cancer-related mortality, fourth after lung cancer, colorectal cancer and breast cancer. (1) Prostate-specific antigen (PSA) and digital rectal examination (DRE) are the main screening tools for prostate cancer screening. (2) PSA testing with or without DRE is a proposed screening strategy in order to diagnose PC in an early localized stage for which a curative treatment is possible. (2) To evaluate the efficacy of PC screening, two large randomized trials have been published. (3). The European Randomized Study of Screening for Prostate Cancer in Europe (ERSPC trial) included a total of 162,243 men between 55 and 69 years of age. The men were randomly assigned to a group offered PSA screening at an average of once every 4 years or to an unscreened control group. During a median follow-up of 9 years, the cumulative incidence of PC was 8.2% in the screened group and 4.8% in the control group. The absolute risk difference was 0.71 deaths per 1000 men. The ERSPC investigators concluded in this study that PSA-based screening reduced the rate of death from PC by 20%. (4) A second trial, the Prostate, Lung, Colorectal, and Ovary (PLCO) trial in the United States was published. The PLCO cancer screening trial randomly assigned 76,693 men to receive either annual screening with prostate-specific antigen (PSA) and digital rectal examination (DRE) or standard care as the control (after a follow-up of 7 years, the incidence of PC per 10,000 person-years was 116 (282 cancers) in the screening group and 95 (232.2 cancers) in the control group (rate ratio: 1.22). The incidence of death per 10,000 person-years were 2.0 (50 deaths) in the screened group and 1.7 (44 deaths) in the control group (rate ratio: 1.13). The PLCO project team concluded that PC-related mortality in screen-detected individuals was very low and not significantly different between the two study groups. (5). The PLCO trial will probably never be able to answer whether or not PSA and DRE screening can influence PC mortality, one likely explanation being the follow up time 7 years that was short compared to the European trial and the sensitivity and specificity of the tests used. Based on this last result, the US preventive services task force (USPSTF) recently issued a recommendation against the use of prostate-specific antigen (PSA) testing for prostate cancer screening. (6) The level of PSA is used as continuous parameter, the higher the value, the more likely the existence of PC. The finding that many men may have PC, despite low levels of serum PSA, has been underscored by recent results from a US prevention study. (7) In a prospective multicentre trial, PC was found on biopsy in 56% of men with a free/total (f/t) PSA<0.10 but in only 8% of men with a f/t PSA>0.25. (8) These data were confirmed in a recent screening test including 27,730 men with a serum PSA concentration between 2.1 and 10 ng/ml. (9) Several pre-analytical and clinical factors may influence the free/total PSA, for example, free PSA is unstable at both 4° C. and at room temperature. For this reason it is urgent to have strong, accurate, sensitive and specific non-invasive test for PC Moreover, the global market for cancer diagnosis is booming since life expectancy is increasing. In developed countries, the percentage of the population older than 60 years was estimated in 2000 to rise from 16.1% in 2000 to 21.4% in 2010. In 2000, the world diagnosis market represented sales of nearly $620 million, with the United States alone accounting for $150 million (www.cowen.com/Research.asp). Implementation of policies for annual screening, age-appropriate cancer screening will revolutionize this market even already many health authorities such as Medicare provide already coverage for an annual PSA test for all men age 50 and older (www.medicare.gov/default.aspx).

SUMMARY

Testing the methylation status of a combination of several genes provides a highly sensitive and highly specific non-invasive tumor diagnosis for early stage prostate cancer. The low-cost tests can use easily obtained samples such as blood, serum, plasma, saliva, or urine.

In one aspect, a highly specific and highly selective method of detecting prostate cancer in a patient includes: obtaining a DNA sample from the patient; and measuring, from the DNA sample, a methylation level in a regulatory region of each of a plurality of genes selected from the group consisting of: GSTP1, CYP27A1, CRYAB, EFS, GSTM2, NBL1, GPRC5B, WFDC2, FCGRT, VAT1, ITM2C, ID4, and C9orf125.

The method can further include comparing the measured methylation level for each of the plurality of genes to a respective threshold methylation level, and, based on the comparisons, detecting the presence or absence of prostate cancer in the patient with high sensitivity and high specificity. The presence or absence of prostate cancer can be detected with a sensitivity of greater than 95% and a specificity of greater than 95%, or with a sensitivity of greater than 99% and a specificity of greater than 99%.

The plurality of genes can include eight or more of the genes listed above. The DNA sample can be obtained from a body fluid, wherein the body fluid is blood, serum, plasma, saliva, urine, stool, tissue, or a combination thereof.

The genes can be the genes of PC Set 1: GSTP1, CYP27A1, CRYAB, EFS, NBL1, GPRC5B, ID4, and C9orf125.

The genes can be the genes of PC Set 2: GSTP1, CYP27A1, CRYAB, EFS, NBL1, VAT1, ID4, and C9orf125.

The genes can be the genes of PC Set 3: GSTP1, CYP27A1, CRYAB, EFS, GPRC5B, WFDC2, ITM2C, and ID4.

The genes can be the genes of PC Set 4: GSTP1, CYP27A1, CRYAB, EFS, GPRC5B, ITM2C, ID4 and C9orf125.

The genes can be the genes of PC Set 5: GSTP1, CYP27A1, CRYAB, EFS, WFDC2, VAT1, ITM2C, and ID4.

The genes can be the genes of PC Set 6: GSTP1, CYP27A1, CRYAB, EFS, VAT1, ITM2C, ID4, and C9orf125.

The genes can be the genes of PC Set 7: GSTP1, CYP27A1, CRYAB, GPRC5B, VAT1, ITM2C, ID4, and C9orf125.

The genes can be the genes of PC Set 8: GSTP1, CYP27A1, EFS, NBL1, GPRC5B, WFDC2, ID4, and C9orf125.

The genes can be the genes of PC Set 9: GSTP1, CYP27A1, EFS, NBL1, WFDC2, VAT1, ID4, and C9orf125.

The genes can be the genes of PC Set 10: GSTP1, CYP27A1, EFS, GPRC5B, WFDC2, ITM2C, ID4, and C9orf125.

The genes can be the genes of PC Set 11: GSTP1, CYP27A1, EFS, WFDC2, VAT1, ITM2C, ID4, and C9orf125.

The genes can be the genes of PC Set 12: GSTP1, CYP27A1, GPRC5B, WFDC2, VAT1, ITM2C, ID4, and C9orf125.

The genes can be the genes of PC Set 13: CYP27A1, CRYAB, EFS, NBL1, GPRC5B, WFDC2, ITM2C, and ID4.

The genes can be the genes of PC Set 14: CYP27A1, CRYAB, EFS, NBL1, WFDC2, VAT1, ITM2C, and ID4.

The genes can be the genes of PC Set 15: CYP27A1, EFS, NBL1, GPRC5B, WFDC2, ITM2C, ID4 and C9orf125.

The genes can be the genes of PC Set 16: CYP27A1, EFS, NBL1, WFDC2, VAT1, ITM2C, ID4, and C9orf125.

The genes can be the genes of PC Set 17: CYP27A1, NBL1, GPRC5B, WFDC2, VAT1, ITM2C, ID4, and C9orf125.

Other aspects, embodiments, and features will be apparent from the following description, the drawings, and the claims.

DETAILED DESCRIPTION

Screening tests for cancer, particularly prostate cancer, based on currently known biomarkers have low sensitivity and low specificity, and few of such tests are evaluated on body fluids. New combinations of biomarkers tested on readily and easily obtained body fluid samples can screen for prostate cancer with high sensitivity and high specificity.

Sensitivity refers to the ability of a screening test to correctly identify true positives. For example, sensitivity can be expressed as a percentage, the proportion of actual positives which are correctly identified as such (e.g., the percentage of test subjects having cancer correctly identified by the test as having cancer). A test with high sensitivity has a low rate of false negatives.

Specificity refers to the ability of a screening test to correctly identify true negatives. For example, specificity can be expressed as a percentage, the proportion of actual negatives which are correctly identified as such (e.g., the percentage of test subjects not having cancer correctly identified by the test as not having cancer). A test with high specificity has a low rate of false positives.

Using a test based on a combination of biomarkers provides a screening test for prostate cancer that can have higher sensitivity, higher specificity, or both higher sensitivity and higher specificity, than tests based on a single biomarker. Preferably a screening test has high levels of both sensitivity and specificity.

Alterations of DNA methylation patterns have been recognized as a common change in human cancers. Aberrant methylation of normally unmethylated CpG islands in or near the promoter region of many genes has been associated with transcriptional inactivation of important genes, including tumor suppressor genes, DNA repair genes, and metastasis inhibitor genes. Therefore, detection of aberrant promoter methylation of cancer-related genes can be an efficient method for the diagnosis, prognosis and/or detection of tumors.

A challenge in identifying DNA methylation patterns is that 5-methylcytosine is indistinguishable from cytosine in its hybridization behavior. The specific reaction of bisulfite with cytosine is therefore useful in investigating DNA methylation. Bisulfite can convert cytosine, but not 5-methylcytosine, to uracil. Uracil corresponds in its base-pairing behavior to thymidine, and thus allows 5-methylcytosine to be differentiated from cytosine using "standard" molecular biological techniques, for example, by amplification and hybridization or sequencing. An older method incorporates the DNA to be investigated in an agarose matrix, through which diffusion and renaturation of the DNA is prevented (bisulfite reacts only on single-stranded DNA) and all precipitation and purification steps are replaced by rapid dialysis (13). Individual cells can be investigated with this method, which illustrates the potential of the method. Of course, previously, only individual regions of up to approximately 3000 base pairs in length have been investigated; a global investigation of cells for thousands of possible methylation analyses is not possible. Of course, this method also cannot reliably analyze very small fragments of small sample quantities. These are lost despite the protection from diffusion through the matrix. Other known methods for detecting 5-methylcytosines are described by Rein et al. (14) and Cottrell (15).

Techniques such as methylation-specific arbitrarily primed PCR, methylated CpG island amplification (MCA), differential methylation hybridization (DMH), and restriction landmark genomic scanning (RLGS) take advantage of methylation-specific restriction enzymes to scan the genome for aberrantly methylated CpG sites. The advantage of these methods is that they directly look for methylation differences. In contrast, candidates can also be identified indirectly using gene expression studies. Gene expression in cell lines treated with 5-azacytidine can be compared to mock-treated cell lines to find genes activated by this de-methylating agent. Some genes in the literature, such as known tumor suppressor genes with CpG islands, are also good candidates.

Further analysis of these marker candidates requires higher throughput methodology. By far the most commonly used assay in research labs is methylation specific-PCR (MSP) or the real-time version (MethyLight). The sample DNA is treated with sodium bisulphite to convert unmethylated cytosines to uracils, while methylated cytosines remain intact. In a gel based MSP assay, one set of primers amplifies the unmethylated version and one set amplifies the methylated version, and the presence of a band on a gel in each reaction determines the methylation state. In the real-time version, amplification with methylation specific primers with or without probes is normalized to the total amount of input DNA to determine the fraction of DNA methylated for each region of interest. Alternative marker analysis methods include oligonucleotide arrays, primer extension, and sequencing.

Biomarkers for prostate cancer were identified in the following way. Public gene expression data for normal and prostate cancer cells was mined to identify genes showing reduced expression levels in prostate cancer cells compared to normal cells. Those genes having reduced expression levels in prostate cancer and CpG promoter islands were further investigated. It is generally known that reduced expression levels for genes with CpG islands is correlated with methylation of the CpG islands. For each of the genes selected for further investigation, a quantitative correlation between expression level and extent of methylation was established. Then, based on that quantitative correlation, a threshold methylation level was established for each gene. The threshold level was set as the highest extent of methylation seen in the normal samples, plus an additional amount, e.g., 5%, 10%, 25%, 33%, etc.

The predictive value of these biomarkers was tested. Again, methylation levels of the genes was determined for a group of normal samples and prostate cancer samples, based on publicly available expression data and the quantitative correlation. For each gene in each sample, the methylation level was compared to the threshold for that gene. If the methylation level was higher than the threshold, that gene was scored as "true" (i.e., predictive of the presence of cancer) for that sample, or, if the methylation level was below the threshold, that gene was scored as "false" (i.e., predictive of the absence of cancer) for that sample. The sensitivity and specificity of several suitably chosen combinations of genes, for correctly predicting the presence or absence of cancer, was then determined based on the scores as defined above.

Thus, in clinical use, the biomarkers can be used in the following way. A DNA sample is obtained from a subject. The DNA sample can derived from any suitable source, including but not limited to blood, serum, plasma, saliva, urine, stool, tissue, or a combination of these. Preferably the DNA sample is derived from a source other than tissue; e.g., blood, serum, plasma, saliva, or urine. The methylation status of several of the biomarker genes identified in the manner described above is then tested by any suitable method for determining the extent of DNA methylation, including but not limited to methylation specific PCR; methylated CpG island amplification; differential methylation hybridization; or restriction landmark genomic scanning. Advantageously, the assessment of methylation is a very stable procedure since, unlike, e.g., measuring mRNA levels, it is much less influenced by experimental parameters. This makes the test efficient for use by any clinical laboratory. The experimentally determined methylation levels for each gene are first compared to their respective threshold levels, and scored as true or false. Advantageously, by using a combination of biomarkers instead of a single marker, the result of the test is both highly sensitive and highly specific. The test can have a sensitivity of no less than 90%, no less than 95%, no less than 96%, no less than 97%, no less than 98%, no less than 99%, or 100%. The test can have a specificity of no less than 90%, no less than 95%, no less than 96%, no less than 97%, no less than 98%, no less than 99%, or 100%. In some instances, both sensitivity and specificity can be no less than 90%, no less than 95%, no less than 96%, no less than 97%, no less than 98%, no less than 99%, or 100%.

DNA methylation plays a substantial role during prostate cancer (PC) development and progression. (10) It induces a change in the transcriptome's profile of epithelial prostate cells. (11) The down-regulation of some genes is induced by the methylation mechanism of CpG islands in their promoters, which inhibits ability of transcription factors to induce the expression of these genes. In addition to having a plausible role in the genomic instability of prostate cells during the PC development, (11) the methylation pattern of a few suitably chosen genes could be used to screen and detect patients having different stages of PC. (12) Most importantly, methylation tests can be done using body fluids such as serum, urine and others.

Using a new computational methodology and available public data, a set of biomarkers—methylated promoter regions of a set of genes—for prostate cancer were identified and then validated in different combinations. The genes were known and some have been previously identified as biomarkers for cancers, but the set, and the combinations of genes from within the set, are new.

Genes whose combined methylation patterns provide 100% sensitivity and 100% specificity for PC diagnosis were identified based on a data set of 32 PC patients and 11 PC-free individuals. Subsets of these genes can also provide 100% sensitivity and 100% specificity for PC diagnosis. These methylation pattern combinations have never been described before for the screening, or diagnosis or prognosis of PC. Transcriptomic data is largely published and made available. However, since methylation technologies are relatively recent, relatively little full methylation public data is available for body fluids as yet. With the goal of identifying a set of methylation-based biomarkers affording non-invasive screening, diagnosis and prognosis of PC, an inferred correlation between gene expression profile in tissue and methylation of these genes in serum was used. This correlation was then applied to assess in silico the sensitivity and specificity of gene markers already published as being methylated in PC. This method allows the identification of a set of genes with a strong diagnostic power when used in combination even at high thresholds of the methylation.

The base set of genes identified is as follows:

Base PC Set: GSTP1, CYP27A1, CRYAB, EFS, GSTM2, NBL1, GPRC5B, WFDC2, FCGRT, VAT1, ITM2C, ID4, and C9orf125.

A test based methylation status of all thirteen of these genes provides 100% sensitivity and 100% specificity for prostate cancer. Tests based on smaller sets (e.g., sets of eight or more) of these genes can also provide 100% sensitivity and 100% specificity for prostate cancer. Those smaller sets include:

PC Set 1: GSTP1, CYP27A1, CRYAB, EFS, NBL1, GPRC5B, ID4, and C9orf125.

PC Set 2: GSTP1, CYP27A1, CRYAB, EFS, NBL1, VAT1, ID4, and C9orf125.

PC Set 3: GSTP1, CYP27A1, CRYAB, EFS, GPRC5B, WFDC2, ITM2C, and ID4.

PC Set 4: GSTP1, CYP27A1, CRYAB, EFS, GPRC5B, ITM2C, ID4 and C9orf125.

PC Set 5: GSTP1, CYP27A1, CRYAB, EFS, WFDC2, VAT1, ITM2C, and ID4.

PC Set 6: GSTP1, CYP27A1, CRYAB, EFS, VAT1, ITM2C, ID4, and C9orf125.

PC Set 7: GSTP1, CYP27A1, CRYAB, GPRC5B, VAT1, ITM2C, ID4, and C9orf125.

PC Set 8: GSTP1, CYP27A1, EFS, NBL1, GPRC5B, WFDC2, ID4, and C9orf125.

PC Set 9: GSTP1, CYP27A1, EFS, NBL1, WFDC2, VAT1, ID4, and C9orf125.

PC Set 10: GSTP1, CYP27A1, EFS, GPRC5B, WFDC2, ITM2C, ID4, and C9orf125.

PC Set 11: GSTP1, CYP27A1, EFS, WFDC2, VAT1, ITM2C, ID4, and C9orf125.

PC Set 12: GSTP1, CYP27A1, GPRC5B, WFDC2, VAT1, ITM2C, ID4, and C9orf125.

PC Set 13: CYP27A1, CRYAB, EFS, NBL1, GPRC5B, WFDC2, ITM2C, and ID4.

PC Set 14: CYP27A1, CRYAB, EFS, NBL1, WFDC2, VAT1, ITM2C, and ID4.

PC Set 15: CYP27A1, EFS, NBL1, GPRC5B, WFDC2, ITM2C, ID4 and C9orf125.

PC Set 16: CYP27A1, EFS, NBL1, WFDC2, VAT1, ITM2C, ID4, and C9orf125.

PC Set 17: CYP27A1, NBL1, GPRC5B, WFDC2, VAT1, ITM2C, ID4, and C9orf125.

EXAMPLES

Several methylated genes described in PC patients were reported in tissue, but high-throughput large cohort results on all these genes are still lacking and few of these genes are investigated for methylation in serum or urine. We collected 548 genes we considered relevant (from articles published in the last two years). Using computational methods and available data, we were be able to predict the sensitivity and the specificity of 199 genes (from this set of 548 genes) in serum, based on their expression profile in tissue of PC patients (32 localized prostate cancer) versus normal subjects (11 either with normal epithelium and stroma or atrophy epithelium) as assessed by a microarray series available in GEO (NCBI, GSE6099). From this set of 199 genes, the 13 genes described in what follows are predicted hypermethylated in PC versus normal, rank among the best p-values using Wilcoxon signed-rank test or among the most discriminating ones based on the threshold, and keep their ability to discriminate under stringent conditions: GSTP1 (Gene ID: 2950), CYP27A1 (Gene ID: 1593), CRYAB (Gene ID: 1410), EFS (Gene ID: 10278), GSTM2 (Gene ID: 2946), NBL1 (Gene ID: 4681), GPRC5B (Gene ID: 51704), WFDC2 (Gene ID: 10406), FCGRT (Gene ID: 2217), VAT1 (Gene ID: 10493), ITM2C (Gene ID: 81618), ID4 (Gene ID: 3400) and C9orf125 (Gene ID: 84302).

The methylation profile of several combinations of these 13 genes keeps the ability to discriminate PC from healthy individuals, with high sensitivity and specificity. Tables 1 and 2 show the methylation status of the 32 patients, defined as "the methylation value is greater or equal to the highest methylation value in normal individuals plus an error margin", for an available dataset. (See legend of Table 1 on how the error margin is measured.) This demonstrates that the combination of these genes has the potential to discriminate patients with PC with a specificity of 100% and a sensitivity of 100%. This is better than the PSA (prostate specific antigen) test largely used that gives high prevalence of false positive and false negative results, (12) or the GSTP1 gene alone that has already reached the clinical validation phase.

TABLE 1

Selected Genes with 5% Threshold

| | GSTP1 | CYP27A1 | CRYAB | EFS | GSTM2 | NBL1 | GPRC5B | WFDC2 | FCGRT | VAT1 | ITM2C | ID4 | C9orf125 |
|---|---|---|---|---|---|---|---|---|---|---|---|---|---|
| 1 | FALSE | TRUE | FALSE | FALSE | FALSE | FALSE | FALSE | FALSE | FALSE | FALSE | FALSE | TRUE | NA |
| 2 | TRUE | FALSE | TRUE | TRUE | FALSE | FALSE | TRUE | FALSE | FALSE | TRUE | NA | FALSE | FALSE |
| 3 | TRUE | FALSE | FALSE | FALSE | FALSE | TRUE | FALSE | FALSE | FALSE | FALSE | TRUE | FALSE | FALSE |
| 4 | TRUE | TRUE | TRUE | FALSE | TRUE | TRUE | TRUE | TRUE | TRUE | TRUE | TRUE | FALSE | TRUE |
| 5 | TRUE | TRUE | TRUE | TRUE | TRUE | TRUE | TRUE | TRUE | TRUE | FALSE | TRUE | TRUE | TRUE |
| 6 | FALSE | TRUE | FALSE | FALSE | FALSE | FALSE | FALSE | FALSE | TRUE | FALSE | FALSE | TRUE | TRUE |
| 7 | TRUE | TRUE | TRUE | TRUE | TRUE | TRUE | TRUE | TRUE | FALSE | FALSE | FALSE | FALSE | FALSE |
| 8 | TRUE | FALSE | FALSE | FALSE | FALSE | TRUE | TRUE | FALSE | FALSE | FALSE | TRUE | FALSE | FALSE |
| 9 | TRUE | TRUE | TRUE | TRUE | TRUE | TRUE | TRUE | FALSE | FALSE | FALSE | TRUE | FALSE | NA |
| 10 | TRUE | TRUE | TRUE | FALSE | TRUE | TRUE | FALSE | TRUE | FALSE | FALSE | TRUE | FALSE | FALSE |
| 11 | TRUE | TRUE | TRUE | TRUE | TRUE | FALSE | FALSE | FALSE | FALSE | TRUE | TRUE | TRUE | FALSE |
| 12 | TRUE | TRUE | TRUE | TRUE | TRUE | TRUE | TRUE | TRUE | FALSE | TRUE | TRUE | TRUE | FALSE |
| 13 | FALSE | FALSE | FALSE | TRUE | FALSE | FALSE | FALSE | FALSE | FALSE | TRUE | FALSE | FALSE | FALSE |
| 14 | FALSE | TRUE | TRUE | FALSE | TRUE | FALSE | TRUE | FALSE | FALSE | FALSE | TRUE | TRUE | TRUE |
| 15 | TRUE | TRUE | TRUE | TRUE | TRUE | TRUE | TRUE | TRUE | TRUE | TRUE | TRUE | FALSE | TRUE |
| 16 | TRUE | TRUE | TRUE | TRUE | TRUE | TRUE | TRUE | TRUE | FALSE | TRUE | FALSE | TRUE |
| 17 | TRUE | TRUE | TRUE | TRUE | TRUE | TRUE | TRUE | FALSE | TRUE | FALSE | TRUE | TRUE | TRUE |
| 18 | TRUE | TRUE | TRUE | TRUE | TRUE | TRUE | TRUE | TRUE | FALSE | FALSE | TRUE | TRUE | TRUE |
| 19 | FALSE | TRUE | FALSE | TRUE | FALSE | FALSE | TRUE | FALSE | FALSE | FALSE | TRUE | TRUE | TRUE |
| 20 | FALSE | FALSE | TRUE | FALSE | FALSE | FALSE | FALSE | TRUE | FALSE | FALSE | FALSE | FALSE | TRUE |
| 21 | FALSE | FALSE | FALSE | TRUE | FALSE | FALSE | FALSE | FALSE | FALSE | FALSE | TRUE | FALSE | TRUE |
| 22 | TRUE | FALSE | FALSE | FALSE | FALSE | TRUE | FALSE | FALSE | FALSE | FALSE | TRUE | TRUE | TRUE |
| 23 | FALSE | FALSE | FALSE | FALSE | FALSE | FALSE | FALSE | FALSE | FALSE | FALSE | FALSE | TRUE | FALSE |
| 24 | FALSE | TRUE | TRUE | TRUE | FALSE | FALSE | TRUE | FALSE | FALSE | FALSE | FALSE | TRUE | TRUE |
| 25 | TRUE | FALSE | FALSE | FALSE | FALSE | TRUE | FALSE | FALSE | FALSE | FALSE | TRUE | TRUE | TRUE |
| 26 | TRUE | TRUE | FALSE | FALSE | TRUE | FALSE | FALSE | TRUE | TRUE | FALSE | FALSE | FALSE | FALSE |
| 27 | FALSE | FALSE | FALSE | FALSE | FALSE | FALSE | FALSE | FALSE | FALSE | FALSE | FALSE | TRUE | FALSE |
| 28 | TRUE | TRUE | TRUE | TRUE | TRUE | TRUE | FALSE | TRUE | FALSE | FALSE | TRUE | TRUE | TRUE |
| 29 | TRUE | FALSE | TRUE | TRUE | TRUE | FALSE | FALSE | TRUE | FALSE | FALSE | TRUE | TRUE | TRUE |
| 30 | TRUE | TRUE | FALSE | TRUE | TRUE | TRUE | FALSE | TRUE | TRUE | TRUE | TRUE | TRUE | FALSE |
| 31 | TRUE | FALSE | TRUE | TRUE | TRUE | TRUE | FALSE | TRUE | TRUE | FALSE | TRUE | NA | TRUE |
| 32 | TRUE | TRUE | TRUE | TRUE | TRUE | TRUE | TRUE | TRUE | TRUE | TRUE | TRUE | TRUE | FALSE |

In Table 1, the data are predicted methylation values from a published study with 32 PC patients versus 11 normal patients. "Threshold" represents the highest methylation value in normal patients with an error margin of 0.05, i.e., 0.05 times the difference between the full methylation value (100% methylation) and the highest methylation value in controls. Values shown in the table are the calls for the 32 PC patients, where "TRUE" represents the serum predicted methylation value being above the threshold, and "FALSE" represents the serum predicted methylation value being below the threshold. "NA" means that data was not available in the study. The combination of 13 biomarkers described in the table afforded 100% sensitivity and specificity when the occurrence of at least one "TRUE" call indicates a diagnosis of having PC.

TABLE 2

Selected Genes with 33% Threshold

| | GSTP1 | CYP27A1 | GSTM2 | EFS | NBL1 | CRYAB | WFDC2 | GPRC5B | VAT1 | FCGRT | ITM2C | ID4 | C9orf125 |
|---|---|---|---|---|---|---|---|---|---|---|---|---|---|
| 1 | FALSE | FALSE | FALSE | FALSE | FALSE | FALSE | FALSE | FALSE | FALSE | FALSE | FALSE | FALSE | NA |
| 2 | FALSE | FALSE | FALSE | TRUE | FALSE | FALSE | FALSE | FALSE | TRUE | FALSE | NA | FALSE | FALSE |
| 3 | FALSE | FALSE | FALSE | FALSE | FALSE | FALSE | FALSE | FALSE | FALSE | FALSE | TRUE | FALSE | FALSE |
| 4 | TRUE | TRUE | TRUE | FALSE | TRUE | TRUE | TRUE | TRUE | TRUE | FALSE | TRUE | FALSE | TRUE |
| 5 | TRUE | TRUE | TRUE | TRUE | TRUE | TRUE | TRUE | FALSE | FALSE | TRUE | TRUE | TRUE | TRUE |
| 6 | FALSE | TRUE | FALSE | FALSE | FALSE | FALSE | FALSE | FALSE | FALSE | TRUE | FALSE | TRUE | TRUE |
| 7 | TRUE | TRUE | TRUE | FALSE | FALSE | TRUE | TRUE | TRUE | FALSE | FALSE | FALSE | FALSE | FALSE |
| 8 | FALSE | FALSE | FALSE | FALSE | FALSE | FALSE | FALSE | TRUE | FALSE | FALSE | TRUE | FALSE | FALSE |
| 9 | TRUE | FALSE | TRUE | TRUE | FALSE | FALSE | FALSE | TRUE | FALSE | FALSE | TRUE | FALSE | NA |
| 10 | TRUE | TRUE | TRUE | FALSE | TRUE | TRUE | FALSE | FALSE | FALSE | FALSE | TRUE | FALSE | FALSE |
| 11 | TRUE | TRUE | TRUE | TRUE | FALSE | TRUE | FALSE | FALSE | FALSE | FALSE | TRUE | FALSE | FALSE |
| 12 | TRUE | TRUE | TRUE | TRUE | TRUE | TRUE | TRUE | FALSE | TRUE | FALSE | TRUE | TRUE | FALSE |
| 13 | FALSE | FALSE | FALSE | FALSE | FALSE | FALSE | FALSE | FALSE | TRUE | FALSE | FALSE | FALSE | FALSE |
| 14 | FALSE | FALSE | FALSE | FALSE | FALSE | FALSE | FALSE | FALSE | FALSE | FALSE | TRUE | TRUE | TRUE |
| 15 | TRUE | TRUE | TRUE | TRUE | TRUE | TRUE | TRUE | TRUE | TRUE | TRUE | TRUE | FALSE | TRUE |
| 16 | TRUE | TRUE | FALSE | TRUE | TRUE | FALSE | FALSE | TRUE | FALSE | FALSE | TRUE | FALSE | TRUE |
| 17 | TRUE | TRUE | TRUE | TRUE | TRUE | FALSE | FALSE | TRUE | FALSE | FALSE | TRUE | TRUE | TRUE |
| 18 | TRUE | FALSE | TRUE | TRUE | TRUE | TRUE | TRUE | FALSE | FALSE | FALSE | TRUE | FALSE | FALSE |
| 19 | FALSE | FALSE | FALSE | FALSE | FALSE | FALSE | FALSE | FALSE | FALSE | FALSE | FALSE | TRUE | TRUE |
| 20 | FALSE | FALSE | FALSE | FALSE | FALSE | FALSE | FALSE | FALSE | FALSE | FALSE | FALSE | FALSE | TRUE |
| 21 | FALSE | FALSE | FALSE | FALSE | FALSE | FALSE | FALSE | FALSE | FALSE | FALSE | FALSE | FALSE | FALSE |
| 22 | TRUE | FALSE | FALSE | FALSE | TRUE | FALSE | FALSE | FALSE | FALSE | FALSE | TRUE | TRUE | FALSE |
| 23 | FALSE | FALSE | FALSE | FALSE | FALSE | FALSE | FALSE | FALSE | FALSE | FALSE | FALSE | TRUE | FALSE |
| 24 | FALSE | TRUE | FALSE | FALSE | FALSE | FALSE | FALSE | FALSE | FALSE | FALSE | FALSE | TRUE | TRUE |
| 25 | TRUE | FALSE | FALSE | FALSE | FALSE | FALSE | FALSE | FALSE | FALSE | FALSE | FALSE | TRUE | TRUE |
| 26 | TRUE | TRUE | FALSE | FALSE | FALSE | FALSE | TRUE | FALSE | FALSE | FALSE | FALSE | FALSE | FALSE |
| 27 | FALSE | FALSE | FALSE | FALSE | FALSE | FALSE | FALSE | FALSE | FALSE | FALSE | FALSE | TRUE | FALSE |
| 28 | TRUE | TRUE | TRUE | TRUE | TRUE | TRUE | TRUE | FALSE | FALSE | FALSE | TRUE | TRUE | TRUE |
| 29 | FALSE | FALSE | TRUE | FALSE | FALSE | FALSE | FALSE | FALSE | FALSE | FALSE | FALSE | TRUE | FALSE |
| 30 | TRUE | FALSE | TRUE | TRUE | FALSE | FALSE | TRUE | FALSE | TRUE | TRUE | TRUE | FALSE | FALSE |
| 31 | TRUE | FALSE | FALSE | TRUE | TRUE | TRUE | FALSE | FALSE | FALSE | TRUE | FALSE | NA | TRUE |
| 32 | TRUE | FALSE | TRUE | TRUE | TRUE | TRUE | TRUE | FALSE | TRUE | TRUE | TRUE | TRUE | FALSE |

In Table 2, parameters were the same as for Table 1, except that a threshold of 0.33 was used.

REFERENCES

Each of the following references is incorporated by reference in its entirety.
(1) Ruddon R W. Cancer Biology Book fourth edition, 2007, p. 62-78. WHO, Cancer Incidence and Mortality Worldwide, Globocan 2008
(2) Lumen N, Fonteyne V, De Meerleert G, Ost P, Villeirs G, Mottrie A, De Visschere P, De Troyer B, Oosterlinck W. Population screening for prostate cancer: An overview of available studies and meta-analysis. Int J Urol. 2011 Nov. 22
(3) Heidenreich A, Bellmunt J, Bolla M, Joniau S, Mason M, Matveev V, Mottet N, Schmid H P, van der Kwast T, Wiegel T, Zattoni F; European Association of Urology. EAU guidelines on prostate cancer. Part 1: screening, diagnosis, and treatment of clinically localised disease. Eur Urol. 2011 January; 59(1):61-71
(4) Schröder F H, Hugosson J, Roobol M J, Tammela T L, Ciatto S, Nelen V, Kwiatkowski M, Lujan M, Lilja H, Zappa M, Denis L J, Recker F, Berenguer A, Määttänen L, Bangma C H, Aus G, Villers A, Rebillard X, van der Kwast T, Blijenberg B G, Moss S M, de Koning H J, Auvinen A; ERSPC Investigators. Screening and prostate-cancer mortality in a randomized European study. N Engl J Med. 2009 Mar. 26; 360(13):1320-8
(5) Andriole G L, Crawford E D, Grubb R L 3rd, Buys S S, Chia D, Church T R, Fouad M N, Gelmann E P, Kvale P A, Reding D J, Weissfeld J L, Yokochi L A, O'Brien B, Clapp J D, Rathmell J M, Riley T L, Hayes R B, Kramer B S, Izmirlian G, Miller A B, Pinsky P F, Prorok P C, Gohagan J K, Berg C D; PLCO Project Team. Mortality results from a randomized prostate-cancer screening trial. N Engl J Med. 2009 Mar. 26; 360(13):1310-9
(6) Vickers A J, Lilja H. Urological cancer: Time for another rethink on prostate cancer screening. Nat Rev Clin Oncol. 2011 Nov. 29
(7) Thompson I M, Pauler D K, Goodman P J, Tangen C M, Lucia M S, Parnes H L, Minasian L M, Ford L G, Lippman S M, Crawford E D, Crowley J J, Coltman C A Jr. Prevalence of prostate cancer among men with a prostate-specific antigen level< or =4.0 ng per milliliter. N Engl J Med. 2004 May 27; 350(22):2239-46
(8) Ilic D, O'Connor D, Green S, Wilt T. Screening for prostate cancer: a Cochrane systematic review. Cancer Causes Control. 2007 April; 18(3):279-85
(9) Kobori Y, Kitagawa Y, Mizokami A, Komatsu K, Namiki M. Free-to-total prostate-specific antigen (PSA) ratio contributes to an increased rate of prostate cancer detection in a Japanese population screened using a PSA level of 2.1-10.0 ng/ml as a criterion. Int J Clin Oncol. 2008 June; 13(3):229-32
(10) Park J Y. Promoter hypermethylation in prostate cancer. Cancer Control, 2010 October; 17(4):245-55. Colombel M, Ricci E, Picard A, Bourrelly E, Groupe Urezus. Hypermethylation and prostate cancer. Prog Urol, 2010 June; 20(6):408-15
(11) Jerónimo C, Bastian P J, Bjartell A, Carbone G M, Catto J W, Clark S J, Henrique R, Nelson W G, Shariat S F. Epigenetics in prostate cancer: biologic and clinical relevance. Eur Urol. 2011 October; 60(4):753-66
(12) Ahmed H. Promoter Methylation in Prostate Cancer and its Application for the Early Detection of Prostate Cancer Using Serum and Urine Samples. Biomark Cancer. 2010 Feb. 18; 2010(2):17-33

(13) Olek A., Oswald J., Walter J. A modified and improved method for bisulphate based cytosine methylation analysis. Nucleic Acids Res. 1996 Dec. 15; 24 (24): 5064-6
(14) Rein T, DePamphilis M L, Zorbas H. Identifying 5-methylcytosine and related modifications in DNA genomes. Nucleic Acids Res. 1998 May 15; 26 (10): 2255-64
(15) Cottrell, S., Molecular diagnostic applications of DNA methylation technology, CLI October 2005.

Other embodiments are within the scope of the following claims.

What is claimed is:

1. A method comprising:
   a) obtaining a DNA sample from a patient, and
   b) measuring, in the DNA sample, a methylation value in a regulatory region of each gene of a set of genes wherein the set consists of GSTP1, CYP27A1, CRYAB, EFS, GSTM2, NBL1, GPRC5B, WFDC2, FCGRT, VAT1, ITM2C, ID4 and C9orf125.

2. The method of claim 1 wherein the sample is blood, serum, plasma, saliva, urine, stool, tissue, or a combination thereof.

* * * * *